US00PP09084P

United States Patent [19]

VandenBerg

[11] Patent Number: Plant 9,084

[45] Date of Patent: Mar. 21, 1995

[54] CHRYSANTHEMUM PLANT NAMED AUSTIN

[75] Inventor: Cornelis P. VandenBerg, Salinas, Calif.

[73] Assignee: Yoder Brothers, Inc., Barberton, Ohio

[21] Appl. No.: 277,286

[22] Filed: Jul. 21, 1994

[51] Int. Cl.[6] ..... A01H 5/00

[52] U.S. Cl. ..... Plt./82.1

[58] Field of Search ..... Plt. 82.1

*Primary Examiner*—Howard J. Locker

*Attorney, Agent, or Firm*—Foley & Lardner

[57] ABSTRACT

A Chrysanthemum plant named Austin particularly characterized by its flat capitulum form; daisy capitulum type; clear white ray floret color; diameter across face of capitulum of 35 to 41 mm when fully opened, when grown as a single stem spray cut mum; flowering response under normal temperatures of 49 to 55 days after start of short days; plant height of 66 to 79 cm with 18 long days prior to start of short days; peduncle length of the first lateral at flowering after removing the apical bud without growth regulator applications of 5 to 8 cm; peduncle length of the fourth lateral at flowering of 8 to 13 cm; and terminal spray formation, with lower laterals being compound.

3 Drawing Sheets

The present invention comprises a new and distinct cultivar of Chrysanthemum, botanically known as *Dendranthema grandiflora,* and referred to by the cultivar name Austin.

Austin, identified as 2899 (90-529003), was originated from a cross made by Cornelis P. VandenBerg in a controlled breeding program in Salinas, Calif., in 1989.

The female parent of Austin was an unnamed seeding identified as 0107 (87-088001), and described as a flat daisy spray cut mum with a white ray floret color; a diameter of capitulum of 35 to 38 mm; a flowering response of 53 to 57 days; a plant height of 97 cm when grown with 14 long days prior to start of short days in Salinas, Calif.; a peduncle length of the first lateral of 13 cm and of the fourth lateral of 18 cm; and a terminal spray formation, with lower laterals being compound. The female parent was discarded from all programs on Sep. 12, 1991.

The male parent of Austin was an unpatented cultivar from Holland, identified as Birkevang, and described as a flat daisy spray cut mum with a yellow ray floret color; flowering response to short days of 53 to 63 days in Salinas, Calif.; a plant height of 81 to 86 cm with 14 to 16 long days prior to start of short days; a peduncle length of the first lateral of 10 to 15 cm and of the fourth lateral of 15 to 18 cm; and a compound spray formation.

Austin was discovered and selected as one flowering plant within the progeny of the stated cross by Cornelis P. VandenBerg in October 1990, in a controlled environment in Salinas, Calif.

The first act of asexual reproduction of Austin was accomplished when vegetative cuttings were taken from the initial selection in December 1990 in a controlled environment in Salinas, Calif., by technicians working under supervision of Cornelis P. VandenBerg.

Horticultural examination of controlled flowerings of successive plantings has shown that the unique combination of characteristics as herein disclosed for Austin are firmly fixed and are retained through successive generations of asexual reproduction.

Austin has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Austin, which in combination, distinguish this Chrysanthemum as a new and distinct cultivar:

1. Flat capitulum form.
2. Daisy capitulum type.
3. Clear white ray floret color.
4. Diameter across face of capitulum of 35 to 41 mm when fully opened, when grown as a single stem spray cut mum.
5. Flowering response under normal temperatures is 49 to 55 days after start of short days.
6. Plant height is 66 to 79 cm with 18 long days prior to start of short days.
7. Peduncle length of the first lateral at flowering after removing the apical bud without growth regulator applications is 5 to 8 cm. Peduncle length of the fourth lateral at flowering is 8 to 13 cm.
8. Terminal spray formation, with lower laterals being compound.

The accompanying photographic drawings show typical inflorescence and leaf characteristics of Austin, with the colors being as nearly true as possible with illustrations of this type.

Sheet 1 is a color photogrpah of Austin grown as a single stem spray cut mum.

Sheet 2 is a black and white photograph of three views of the inflorescence of Austin.

Sheet 3 is a black and white photograph showing the upper and under sides of the leaves of Austin at 3 stages of development (mature, intermediate and immature).

In Sheets 2 and 3 a measuring tape in centimeters has been added.

Of the commercial cultivars known to the inventor, the most similar in comparison to Austin is the cultivar identified as Banjo, a commercial but unpatented cultivar. Reference is made to attached Chart A, which compares certain characteristics of Austin to the same characteristics of Banjo.

Similar traits are ray floret color and capitulum form and type. Austin has a smaller diameter of capitulum, a faster flowering response to short days, a shorter plant height and shorter peduncles when compared with Banjo. Austin also shows a compound spray formation of the lower laterals, while Banjo shows little to no compounding of the lower laterals.

In the following description color references are made to the Royal Horticultural Society Colour Chart. The color values were determined on plant material grown as a single stem spray cut mum in Salinas, Calif. on Dec. 16, 1993.

Classification:

*Botanical.*—*Dendranthema grandiflora* cv Austin.

*Commercial.*—Daisy spray cut mum.

INFLORESCENCE

A. Capitulum:

*Form.*—Flat.

*Type.*—Daisy.

*Diameter across face.*—35 to 41 mm when fully opened.

B. Corolla of ray florets:

*Color* (*general tonality from a distance of three meters*).—Clear white.

*Color* (*upper surface*).—Clear white.

*Color* (*under surface*).—Clear white.

*Shape.*—Straight, flat.

C. Corolla of disc florets:

*Color* (*mature*).—14A.

*Color* (*immature*).—144B.

D. Reproductive organs:

*Androecium.*—Present on disc florets only; no pollen.

*Gynoecium.*—Present on both ray and disc florets.

PLANT

A. General appearance:

*Height.*—66 to 79 cm when grown in Salinas with 18 long days prior to start of short days.

B. Foliage:

*Color* (*upper surface*).—147A.

*Color* (*under surface*).—147B.

*Shape.*—See photograph.

CHART A

COMPARISON OF AUSTIN AND BANJO

| CHARACTERISTIC | AUSTIN | BANJO |
|---|---|---|
| Ray floret color | Clear white | Clear white |
| Capitulum form and type | Flat daisy | Flat Daisy |
| Diameter across face of of capitulum | 35 to 41 mm | 38 to 48 mm |
| Flowering response | 49 to 55 days | 52 to 58 days |
| Plant height | | |
| with 18 long days | 66 to 79 cm | |
| with 11 to 14 long days | | 89 to 107 cm |
| Peduncle length: | | |
| First lateral | 5 to 8 cm | 10 to 13 cm |
| Fourth lateral | 8 to 13 cm | 10 to 15 cm |
| Spray formation | Terminal with lower laterals compound | Terminal |

COMPARISONS MADE OF PLANTS GROWN AS SINGLE STEM SPRAY CUT MUMS IN SALINAS, CALIFORNIA

I claim:

1. A new and distinct Chrysanthemum plant named Austin, as described and illustrated.

* * * * *

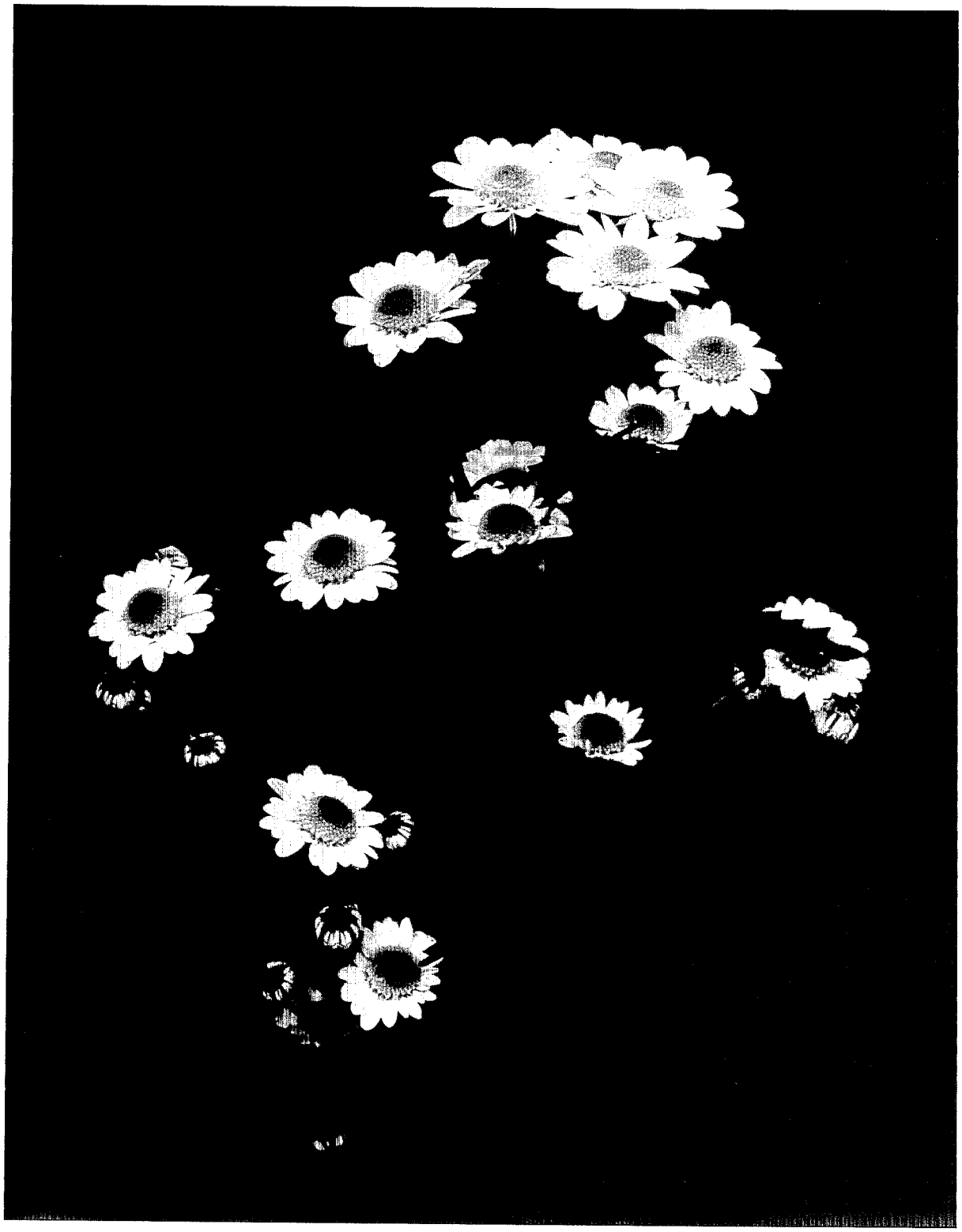

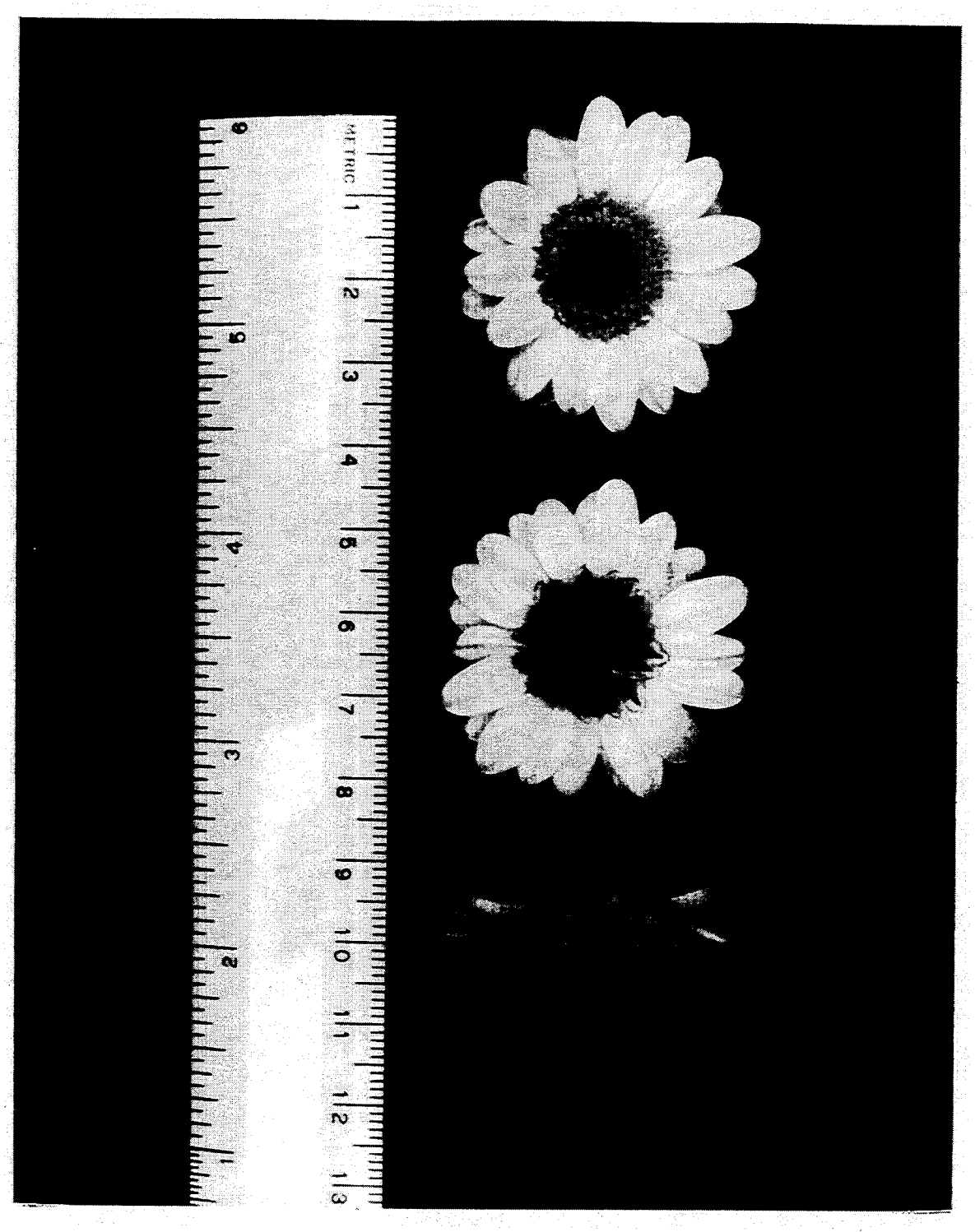
METRIC

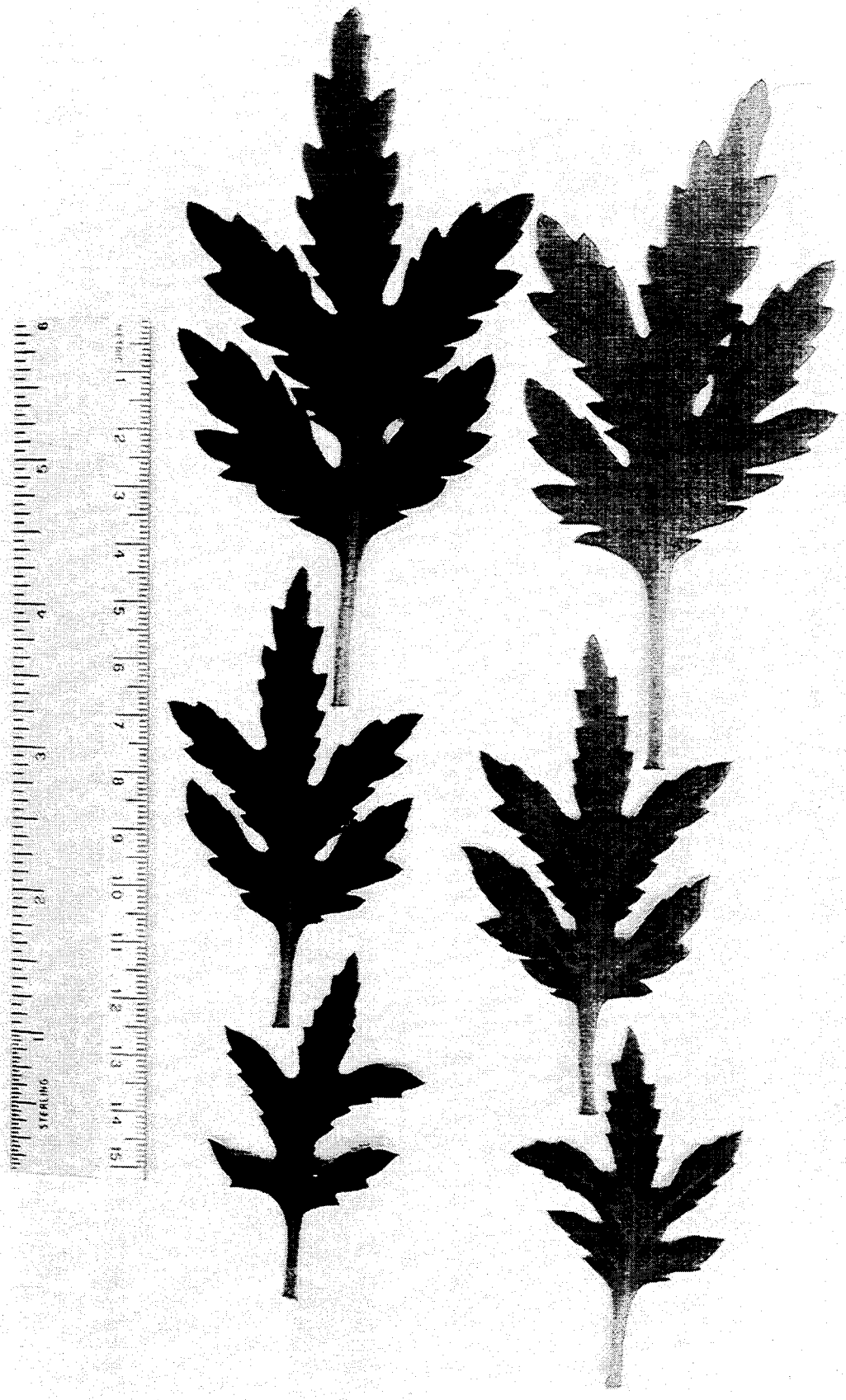
STEROLOG